US011241204B2

(12) United States Patent
Spartiotis et al.

(10) Patent No.: US 11,241,204 B2
(45) Date of Patent: Feb. 8, 2022

(54) WIRELESS INTRA ORAL SENSOR HOLDER

(71) Applicant: ATHLOS OY, Espoo (FI)

(72) Inventors: Konstantinos Spartiotis, Espoo (FI); George Gennadios, Glyfada (GR); Vasileios Grammatikakis, Sawtry (GB)

(73) Assignee: ATHLOS OY, Espoo (FI)

( * ) Notice: Subject to any disclaimer, the term of this patent is extended or adjusted under 35 U.S.C. 154(b) by 0 days.

(21) Appl. No.: 17/264,500

(22) PCT Filed: Aug. 8, 2019

(86) PCT No.: PCT/FI2019/050579
§ 371 (c)(1),
(2) Date: Jan. 29, 2021

(87) PCT Pub. No.: WO2020/030854
PCT Pub. Date: Feb. 13, 2020

(65) Prior Publication Data
US 2021/0290188 A1    Sep. 23, 2021

(30) Foreign Application Priority Data

Aug. 8, 2018   (FI) .................................... 20187101

(51) Int. Cl.
*A61B 6/14*   (2006.01)
*H04N 5/32*   (2006.01)

(52) U.S. Cl.
CPC .............. *A61B 6/145* (2013.01); *H04N 5/32* (2013.01); *A61B 2560/0214* (2013.01)

(58) Field of Classification Search
CPC ... A61B 6/145; A61B 2560/0214; H04N 5/32
See application file for complete search history.

(56) References Cited

U.S. PATENT DOCUMENTS

| | | | | |
|---|---|---|---|---|
| 6,190,042 B1* | 2/2001 | Dove | ..................... | A61B 6/145 |
| | | | | 378/167 |
| 10,327,719 B2* | 6/2019 | Tomkoria | ............... | A61B 6/145 |

(Continued)

FOREIGN PATENT DOCUMENTS

| | | |
|---|---|---|
| EP | 3 120 775 | 12/2009 |
| EP | 3 185 073 | 6/2017 |

(Continued)

OTHER PUBLICATIONS

International Search Report issued in International Application No. PCT/FI2019/050579, dated Oct. 29, 2019, 4 pages.

(Continued)

*Primary Examiner* — David P Porta
*Assistant Examiner* — Mamadou Faye
(74) *Attorney, Agent, or Firm* — Nixon & Vanderhye

(57) ABSTRACT

Disclosed is an intraoral dental x-ray imaging sensor holder for Wireless IntraOral x-ray imaging Sensors ("WIOS"). The holder secures in place the WIOS from the hump on the backside of the WIOS corresponding to the battery. The holder with the WIOS attached can be painlessly and comfortably positioned inside the dental arch, since there are no brackets holding the WIOS from its edges, but instead from the battery hump. Additionally, the WIOS can be secured on the holder in reverse (rotated by 180 degrees) thus adding flexibility and versatility during intraoral x-ray imaging.

17 Claims, 22 Drawing Sheets

(56) References Cited

U.S. PATENT DOCUMENTS

| | | |
|---|---|---|
| 2002/0076002 A1 | 6/2002 | Eppinger et al. |
| 2004/0188625 A1* | 9/2004 | Schulze-Ganzlin ..... A61B 6/14 |
| | | 250/370.09 |
| 2005/0220272 A1 | 10/2005 | Glazer |
| 2005/0226390 A1 | 10/2005 | Ihalainen |
| 2008/0298543 A1 | 12/2008 | Razzano |
| 2010/0254518 A1 | 10/2010 | Khouri |
| 2010/0329431 A1 | 12/2010 | Augais |
| 2011/0299663 A1 | 12/2011 | Steward, Jr. |
| 2015/0139405 A1 | 5/2015 | Laude |
| 2017/0079602 A1 | 3/2017 | Lim et al. |
| 2017/0086760 A1 | 3/2017 | Kim et al. |
| 2017/0202526 A1* | 7/2017 | Palermo .................. A61B 6/04 |
| 2018/0064406 A1* | 3/2018 | Pascal .................. A61B 6/4208 |
| 2018/0160991 A1 | 6/2018 | Chun et al. |
| 2018/0206802 A1* | 7/2018 | Heo ....................... G03B 42/00 |
| 2018/0214099 A1 | 8/2018 | Martin |

FOREIGN PATENT DOCUMENTS

| | | |
|---|---|---|
| JP | 2010-162326 | 7/2010 |
| WO | 2006/004528 | 1/2006 |
| WO | 2012/060063 | 5/2012 |

OTHER PUBLICATIONS

Written Opinion of the ISA for PCT/FI2019/050579, dated Oct. 29, 2019, 8 pages.
Office Action for FI20187101, dated Apr. 8, 2019, 10 pages.

* cited by examiner

WIRELESS INTRA ORAL SENSOR HOLDER

This application is the U.S. national phase of International Application No. PCT/FI2019/050579 filed 8 Aug. 2019, which designated the U.S. and claims priority to FI Application No. 20187101 filed 8 Aug. 2018, the entire contents of each of which are hereby incorporated by reference.

FIELD OF THE INVENTION

The present invention relates to intraoral x-ray imaging sensors and more specifically to wireless intraoral imaging sensors (WIOS).

BACKGROUND OF THE INVENTION

Intraoral imaging utilizing sensors has the advantage of immediate (less than 10 seconds) display on the computer screen of the diagnostic intraoral images as opposed to the use of phosphor plates which require a reader for extracting the digital image. Additionally, several images can be taken one after the other to create a full mouth series or a bite wing series. An intraoral x-ray imaging sensor has typically a detector to convert incoming x-rays to either visible light (indirect conversion) or to electric pulse (direct conversion). Examples of indirect conversion intraoral detector include cesium iodide (CsI) deposited on a fiber optic plate. Examples of direct conversion intraoral detectors include silicon (Si), cadmium telluride (CdTe) and mercuric iodide ($HgI_2$), although none of the direct conversion intraoral sensors has reached the market yet. The light in the case of the indirect conversion sensors and the electric current in the case of direct conversion intraoral sensors goes to a readout Complementary Metal Oxide Semiconductor (CMOS) substrate which either detects the light or stores the electric current. The CMOS is then readout either in analog mode or in digital mode with an analog to digital converter resident on the CMOS itself. In older versions of intraoral sensors the readout substrate was comprising a Charged Coupled Device (CCD).

The available intraoral sensors have a cable attached to the backside of an encapsulated sensor, which comes out of the mouth and is connected to a readout box further down, or to an input port of a computer. The cable carries the signals to control the electronics of the intraoral sensor and the CMOS and also carry the output of the CMOS for display to a monitor.

Additionally, in some models the cable is connected nearby to a device for initial display of the image and further down streaming from the nearby device via wireless link to a main computer or other diagnostic station.

The intraoral sensor and the cable are mounted on a holder which is positioned inside the mouth. Available holders grab the intraoral sensor from either the long sides or the short sides. The holding bracket is causing discomfort and in many cases sheer pain as it is then pushed against the mandibular, maxillary or anterior tissue. Additionally, the holding brackets available are in many cases obstructing incoming x-rays from entering the x-ray window of the intraoral sensor and also by the way the brackets hold the intraoral sensor (i.e., holding from the sides) the inactive area is increased.

SUMMARY

It has been observed that current intraoral sensor holders made for intraoral sensors with a cable (wire) suffer from one or more of the following deficiencies:

a) They cause pain and discomfort, because in most case the sensor is held with brackets around the edges and these brackets come into contact with the sensitive human tissue;
b) They introduce a layer of material on the path of the incoming x-rays, i.e. valuable x-ray signal is lost;
c) They increase the inactive area The assignee of the current invention is also the holder of a new generation of intraoral sensors, namely wireless intraoral sensors. These wireless intraoral sensors are described in detail in Finnish patent application 20187036 filed on 16 Mar. 2018, Finnish patent application 20187040 filed on 20 Mar. 2018 and Finnish patent application 20187045 filed on 27 Mar. 2018, all of which are incorporated herein by reference. This new generation of intraoral sensors offer great many advantages. It would be desirable to match the advantages of such wireless intraoral sensors with a new holder approach that mitigates the deficiencies and problems of the prior art holders.

The presence of the cable coming out of the mouth is creating discomfort to the patients and makes positioning of the sensor difficult. In many cases the discomfort and the difficulty in positioning leads to faulty exposures and as a result a new exposure is required.

Additionally, the cable and in particular the area where the cable comes out from the back of the sensor is one of the main failure points of the sensor. The connection of the cable to the backside of the sensor needs to withstand stress and strain in everyday use with pull, push and rotational forces applied to the contact. Quite often the cable close to or at the backside contact will break. As a result, the connection needs to be reinforced causing a relatively large hump on the back of the sensor in all three dimensions. This large hump causes more inconvenience to the patient.

It would therefore be very desirable to have a completely wireless, compact and robust intraoral sensor.

It has been observed that a viable wireless intraoral sensor may fail for mainly the following reasons:

The wireless sensor is powered by a single use battery that will last a few exposures and will have to be disposed afterwards. A new battery will have to be used subsequently A wireless link is not reliable and data is lost all too often, creating the need of additional exposure The sensors, although wireless, are bulky mainly due to the use of indirect conversion scintillator with a thick fiber optic plate, single use thick battery packs and bulky wireless electronics The sensors are fragile and sensitive. A wireless sensor is even more likely to be dropped on the floor accidentally and consequently it is even more imperative that a wireless sensor is robust and withstands shocks.

Furthermore, the wired sensor discomfort is compounded by sensor holder designs that, due to the cable on the backside, grab the sensor from the sides. This, as mentioned already, creates pain when the brackets come into contact with human tissue. In many cases the brackets holding the sensor from its edges introduce a plastic or other type of layer on the front of the sensor, i.e., the direction of incidence of the x-rays, reducing the signal and "wasting" useful radiation. Finally bracket solutions holding the sensor from the sides (long or short edges), increase the inactive area. This means that in order to image the mandibular or maxillary posterior teeth additional pressure is applied to push the sensor towards the roots of the teeth with the holder brackets making contact with the tissue. Again, more pain and discomfort is caused because of this.

It has been observed that it would be extremely desirable and a major advancement in the field of intraoral x-ray imaging to be able to provide a completely wireless intraoral sensor, i.e. an intraoral sensor without a cable coming off the back of the sensor that is inserted to the human mouth and to match this with an innovative holder design that mitigates the pain and discomfort caused by prior art holders. To that effect embodiments of the present invention provide a wireless intraoral x-ray imaging sensor holder which holds the sensor in place by locking, clipping or generally attaching to the sensor from the battery-hump on the backside (opposite face) of the sensor's active area, without any brackets grabbing the sensor from its short or long edges (sidewalls). The holder attaches to and holds the sensor from the hump whereas the hump is the part of the encapsulation covering the rechargeable compact battery suitably positioned with an adequate distance from the edge of the Printed Circuit Board (PCB) (or ceramic). This allows the encapsulation of the battery on the backside to not be in contact with the edges of the sensor thus providing a comfortable and easy way to position the sensor inside the mouth once the sensor is attached to the holder. Because the holder is attached to the battery-hump, the edges (sidewalls) of the sensor are free of any brackets and the sensor feels comfortable and pain free, even when coming to contact with the human tissue.

Furthermore because there is no cable to complicate positioning, the wireless intraoral sensor can be mounted on the holder in more than one positions, for example two separate positions with the two positions having 180 degrees rotation with respect to one another. This means that both towards the distal or towards the mesial areas inside the cranial cavity access and imaging is optimal with the truncated corners of the sensor and the side with the maximum active area always pointed towards the critical diagnostic direction.

In accordance with a first aspect of the current invention we provide a wireless intraoral x-ray imaging sensor holder, comprising a bite block which attaches to a hump on the back of said wireless intraoral x-ray imaging sensor.

In certain embodiments, said hump corresponds to the encapsulation of battery of said wireless intraoral x-ray imaging sensor.

In accordance with another aspect of the current invention said holder comprises a holder handle, an x-ray tube alignment ring and a bite block.

In certain embodiments, said holder handle comprises separately a first part and a second part, whereas said first part can be selectively used individually for reducing the overall length of handle or in the alternative said first part and second part are selectively used combined together for increasing the overall length of handle.

Furthermore, in yet another aspect of the current invention we provide a wireless intraoral x-ray imaging sensor system, comprising:
  a wireless intraoral x-ray imaging sensor comprising a battery resulting to a hump on the backside of said wireless intraoral x-ray imaging sensor; and
  a wireless intraoral x-ray imaging sensor holder as previously mentioned, for securing and positioning said wireless intraoral x-ray imaging sensor with respect to the dental arch, characterized in that said holder secures in place said wireless intraoral x-ray imaging sensor from the hump.

In certain embodiments, said wireless intraoral x-ray imaging sensor of the intraoral x-ray imaging sensor system is selectively secured onto said wireless intraoral x-ray imaging sensor holder with two or more orientations.

In certain embodiments, said wireless intraoral x-ray imaging sensor is secured onto said wireless intraoral x-ray imaging sensor holder selectively, with two orientations, 180 degrees with respect to each other.

In certain embodiments there is provided a wireless intraoral x-ray imaging sensor (WIOS) holder that secures in place the WIOS from the hump on the backside of the WIOS corresponding to the battery. The holder with the WIOS attached can be painlessly and comfortably positioned inside the dental arch, since there are no brackets holding the WIOS from its edges, but instead from the battery hump. Additionally, the WIOS can be secured on the holder in reverse (rotated by 180 degrees) thus adding flexibility and versatility during intraoral x-ray imaging.

BRIEF DESCRIPTION OF THE DRAWINGS

In the following, the invention is presented in detail by referring to the attached drawings, where.

DETAILED DESCRIPTION OF THE INVENTION

With reference now to the accompanying figures we describe in detail the invention and the preferred embodiments.

Figure 1A:
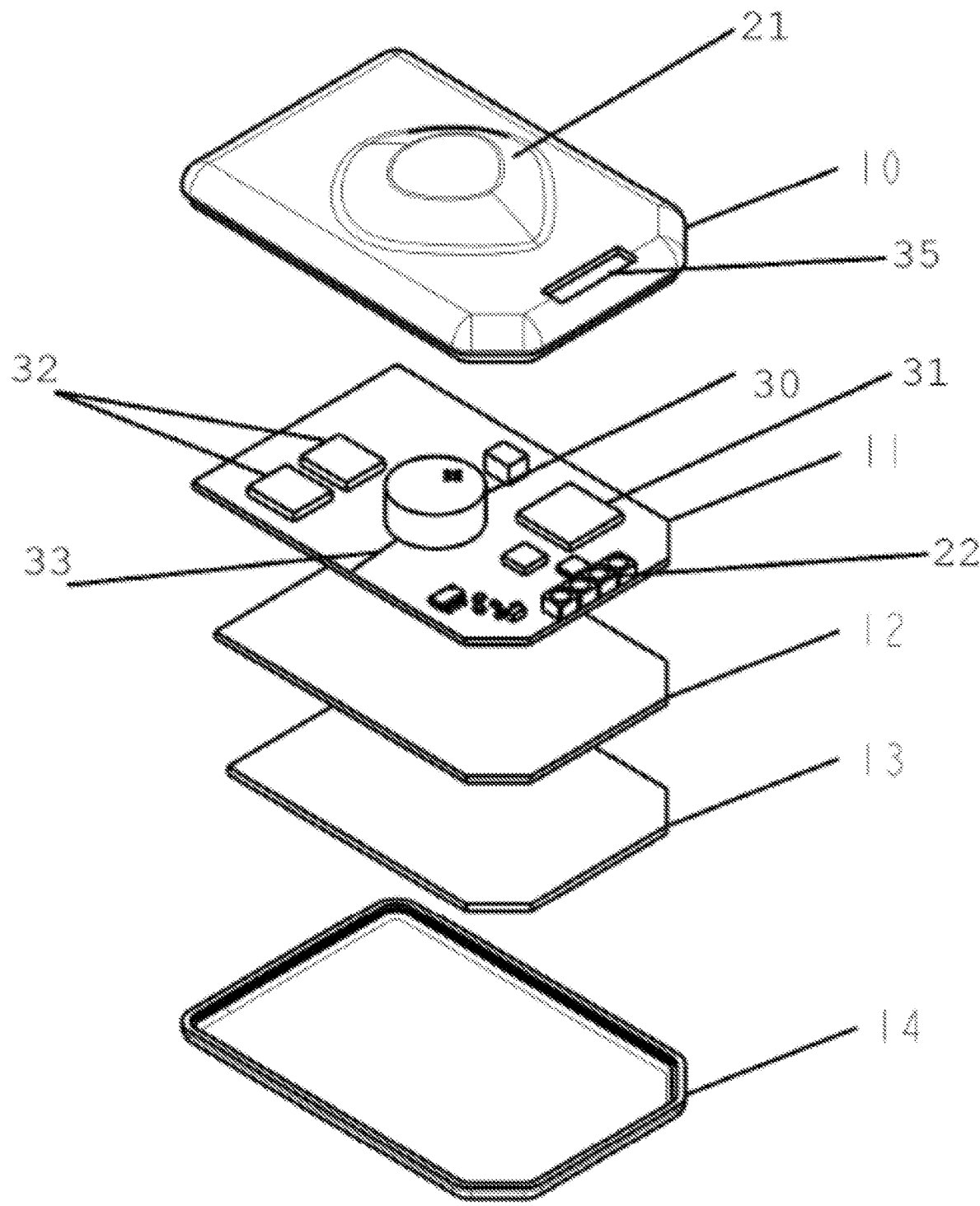
FIG. 1a shows a wireless intraoral sensor with a blow-up view of the various parts and components of the sensor in accordance with certain embodiments.

With reference now to FIG. 1a, a direct conversion wireless intraoral sensor comprises a Silicon (Si) direct conversion semiconductor detector substrate 13 bonded to a readout substrate 12 which is an Application Specific Integrated Circuit (ASIC). Typically such readout ASIC substrates comprise Complementary Metal Oxide Semiconductor (CMOS). The Si-CMOS hybrid has an active area sensitive to incoming x-rays. In dental intraoral x-ray imaging there are worldwide three different active area sensors, independently to what is the detector material or detection technique. The three different intraoral sensor categories are: a) size 0 with active area 15-18 mm×20-24 mm, b) size 1 with active area 19-23 mm×28-32 mm and c) size 2 with active area 24-27 mm×33-36 mm.

With reference to FIG. 1a, we depict a size 2 wireless intraoral x-ray imaging sensor. The Si-CMOS is glued and wire bonded onto a further substrate 11 which is typically a Printed Circuit Board (PCB) made of FR4 multilayers or in the alternative a ceramic type of further substrate, for example 96% $Al_2O_3$. The further substrate 11 carries on the opposite phase to the one where the Si-CMOS hybrid is mounted all the external/peripheral components needed to control and readout the CMOS 12. In accordance with certain embodiments it comprises a Microcontroller Unit (MCU) 31, and in accordance with certain embodiments external memory cells 32 with sufficient capacity to hold a full post processed image. In accordance with certain embodiments the further substrate 11 also contains a DC battery 30 which is rechargeable and having a capacity of 5 mAh or more, preferably a capacity between 5 mAh-50 mAh to be able to provide sufficient energy but also be compact. The operating voltage of the rechargeable battery 30 is between 2.5 Volts and 5 Volts. In accordance with certain embodiments the rechargeable battery 30 must have a lifetime of at least 50 cycles, more preferably 100 cycles and most preferably 300 cycles or more. The rechargeable battery 30 should be of an appropriate shape that allows compact encapsulation. It is critical that after the encapsulation the hump on the back of the wireless intraoral sensor is not too close to the edge of the sensor as this would cause discomfort and make positioning harder. In accordance with certain embodiments the rechargeable battery 30 is of a cylindrical shape with a diameter of 15 mm or less and height of 8 mm or less. More preferably the rechargeable battery 30 has diameter of 10 mm or less and height of 4 mm or less. Furthermore the layout of the further substrate 11 is such that allows the positioning 33 of the battery 30 to be at least 2 mm, better at least 3 mm to 5 mm and even better at least 7 mm inwards from the nearest edge 33 of the further substrate 11. For embodiments of the holder invention that follow it is important and beneficial that the battery is positioned symmetrically on the x or y dimension of the substrate 11. With this electromechanical arrangement the backside of the encapsulation 10 will have a hump 21 which is rather centered or at least not reaching the edge of the encapsulation cover 10. Preferably, for embodiments of the holder invention to be implemented optimally the battery hump should be centered along the short dimension of the wireless intraoral x-ray imaging sensor. It is noted that the back face of the wireless intraoral imaging sensor is generally flat, except for the hump in the encapsulation necessitated from to the presence of the battery. In accordance with certain embodiments we are exploiting the presence of the battery hump to provide for a locating feature with a mounting/locking structure from where the Wireless IntraOral Sensor ("WIOS") is securely held on the holder.

Figure 1B:
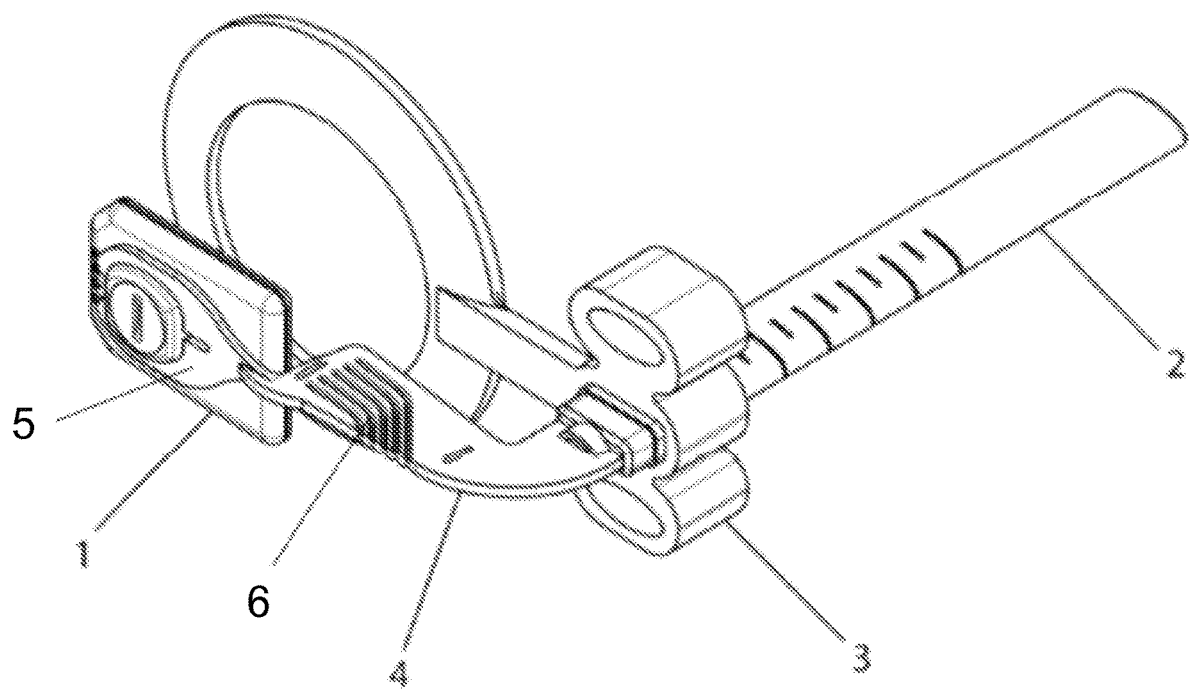
FIG. 1b shows a bite wing holder holding the wireless intraoral sensor in accordance with certain embodiments.
Figure 1C:
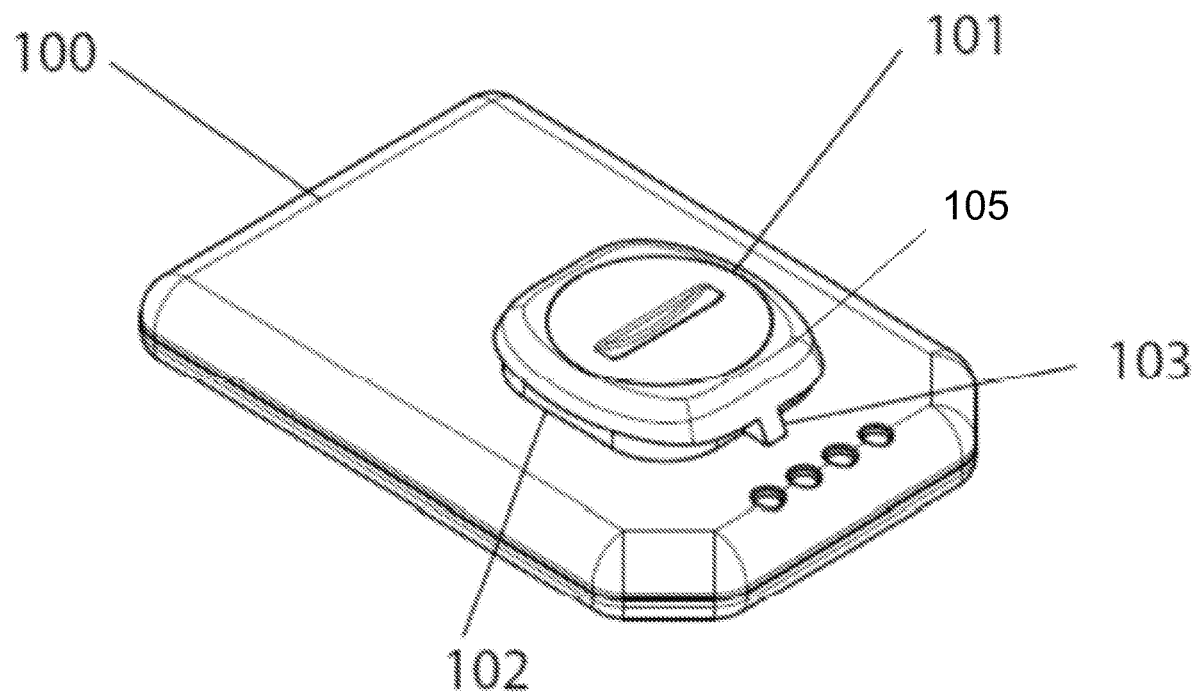
FIG. 1c shows a close-up view of an encapsulated wireless intra oral sensor including the battery hump in accordance with certain embodiments.

With reference now to FIG. 1c, we show in more detail the back side of the encapsulated WIOS in accordance with certain embodiments. The back side 100 is generally flat. The battery hump 105 is provided with a removable cover part 101 that can be screwed/unscrewed in order to replace the battery when needed. In accordance with certain embodiments the battery hump 105 is provided with a groove 102 around the circumference. The holder will hold the sensor from the hump utilizing the groove 102. Furthermore we provide a locating feature 103 which is used to allow the holder to lock onto the sensor in one of two rotational positions (at 0 deg or with 180 deg rotation).

With reference to FIG. 1b, we show the WIOS 1 mounted onto the bitewing holder according to certain embodiments. The bite wing holder comprises the following parts: a) the handle 2, b) the x-ray tube alignment ring 3 which has three separate locations for the handle to slide through and c) the bite block 4 which includes a bracket part 5 that clips onto the groove 102 provided on the WIOS hump 105, guided by the location feature 103 which slides into a corresponding recess provided on 5. It is to be noted that no part of the holder is in contact with the edges of the WIOS 1, thus the entire active area (front face) and the edges of WIOS 1 are free of any holder parts or brackets, thus making the positioning of the WIOS 1 painless and optimal.

Figure 2:
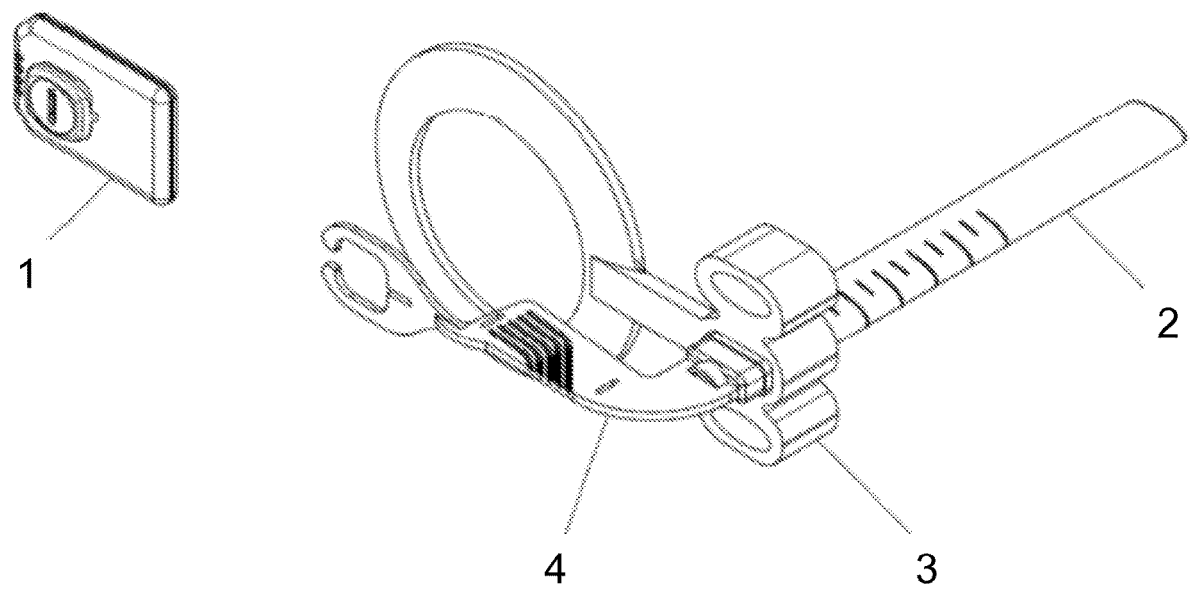
FIG. 2 shows the bite wing holder and separately the wireless intraoral sensor in accordance with certain embodiments.
Figure 3:
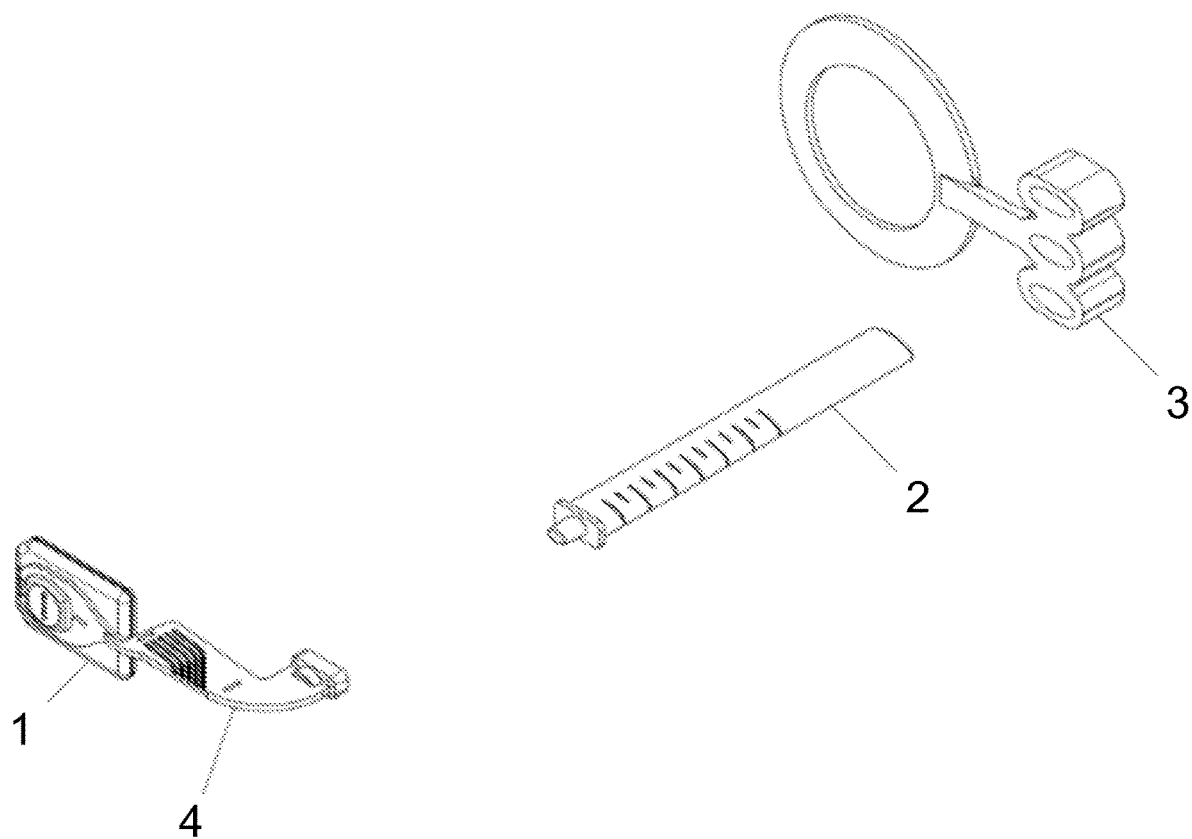
FIG. 3 shows the bite wing holder of the wireless intraoral sensor disassembled to its various parts in accordance with certain embodiments.

In FIG. 2 we show the same bite wing holder where the WIOS 1 has been removed from the holder In FIG. 3 we show the bite wing holder disassembled to its three individual parts with the bite wing block 4 attached to the WIOS 1. The handle 2 is provided with grooves to allow the positioning of the x-ray tube alignment ring to a certain distance from the WIOS 1.

Figure 4:
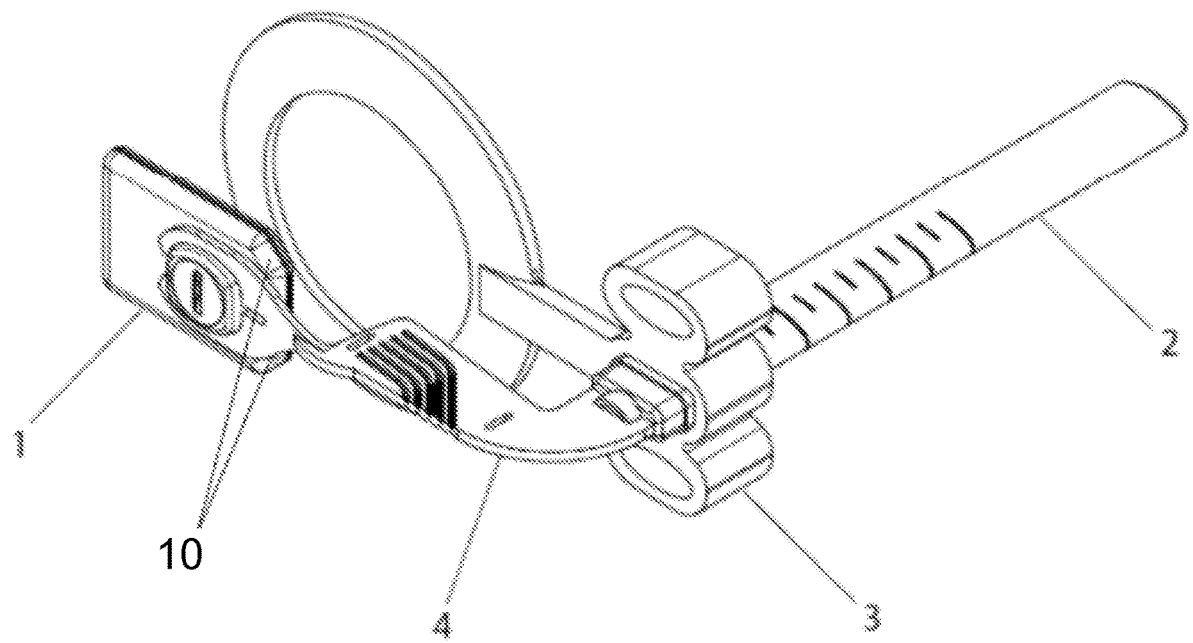
FIG. 4 shows the bite wing holder holding the wireless intraoral sensor rotated 180° (180 degrees; i.e. the truncated corners are pointing inbound and towards the bite block) in accordance with certain embodiments.

FIG. 4 shows the same bite wing holder as is shown in FIG. 3, except that WIOS 1 is rotated 180 deg prior to mounting onto the holder. In this case the truncated corners 10 of FIG. 1a and also shown in FIG. 4 are pointing towards the bite block. This possibility to mount the WIOS 1 in either direction offers great advantages because it allows the WIOS to be positioned with the maximum active area and the truncated corners optimally pointing towards the distal or mesial area inside the cranial/mouth cavity depending on the diagnostic area of interest. By "mesial" we mean the direction towards the anterior midline in a dental arch, as opposed to "distal", which refers to the direction towards the gingiva beyond the tooth furthest from the anterior midline (the 'most posterior tooth' or last tooth) in each quadrant.

Figure 5:
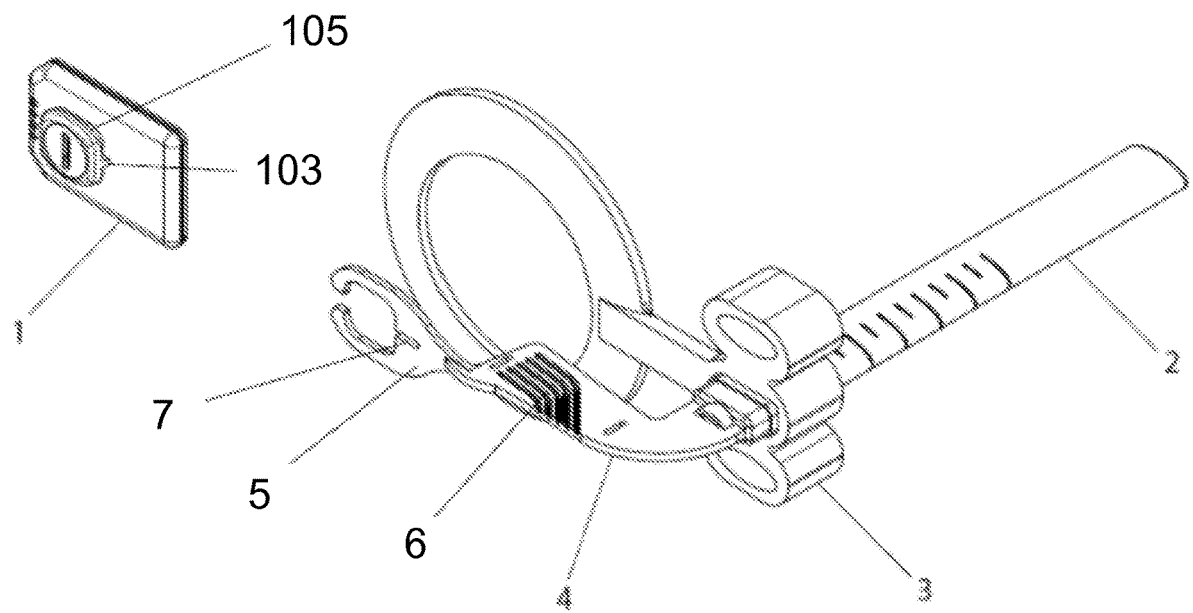
FIG. 5 shows the bite wing holder and the wireless intraoral sensor in accordance with certain embodiments.

FIG. 5 shows the WIOS 1 separated from the bite wing holder. The bite block 4 is provided with ridges 6 which help when biting to position and secure the bite block inside the mouth. Notably FIG. 5 shows the bracket 5 which is for sliding and clipping onto the WIOS 1, at the battery hump position 105 guided and secured with the grooves 102 on the battery hump 105 and the location feature 103. Shown in FIG. 5 is the corresponding recess 7 on the bite block 4 which is provided to match the locating feature 103.

Figure 6:
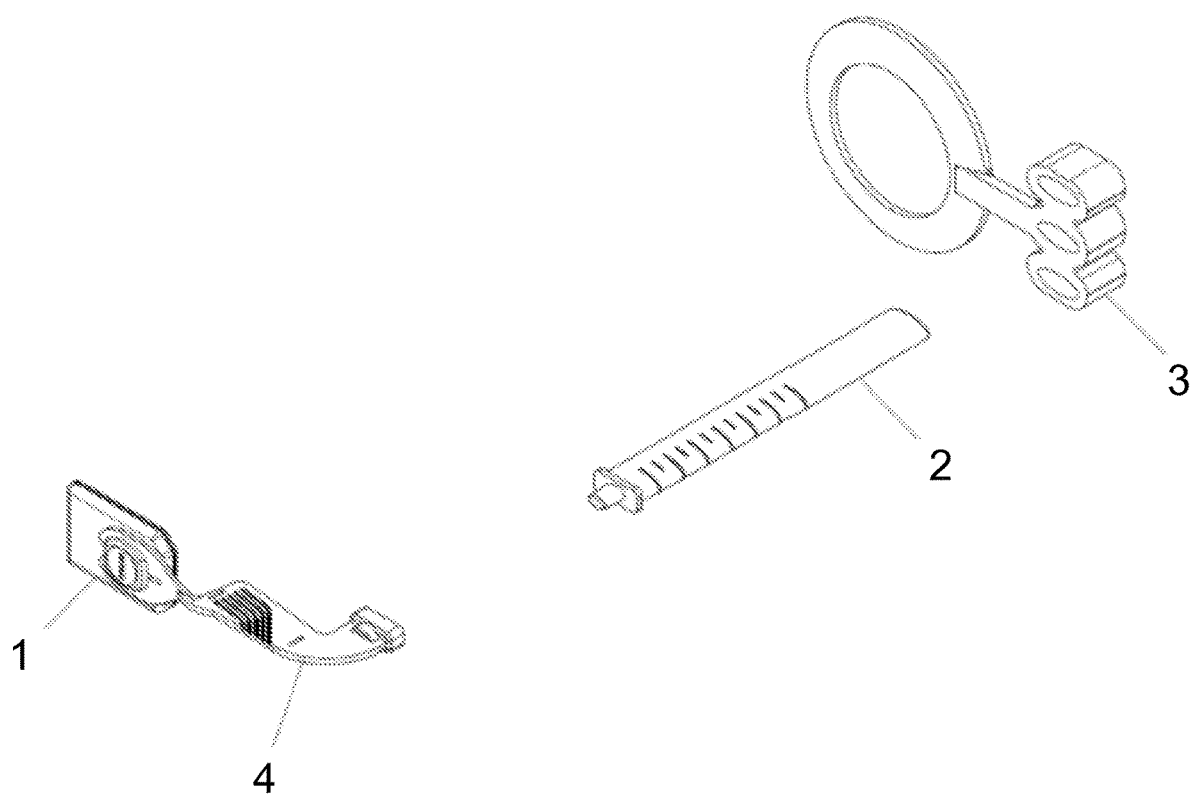
FIG. 6 shows the bite wing holder, of the wireless intraoral sensor rotated 180° (180 degrees; i.e. the truncated corners are pointing inbound and towards the bite block), disassembled to its various parts in accordance with certain embodiments.

FIG. 6 is similar to FIG. 3 with the WIOS 1 reversed 180 deg and offering the flexibility and versatility in diagnostic imaging whether of interest is more the distal or mesial pat of the dental arch.

Figure 7:
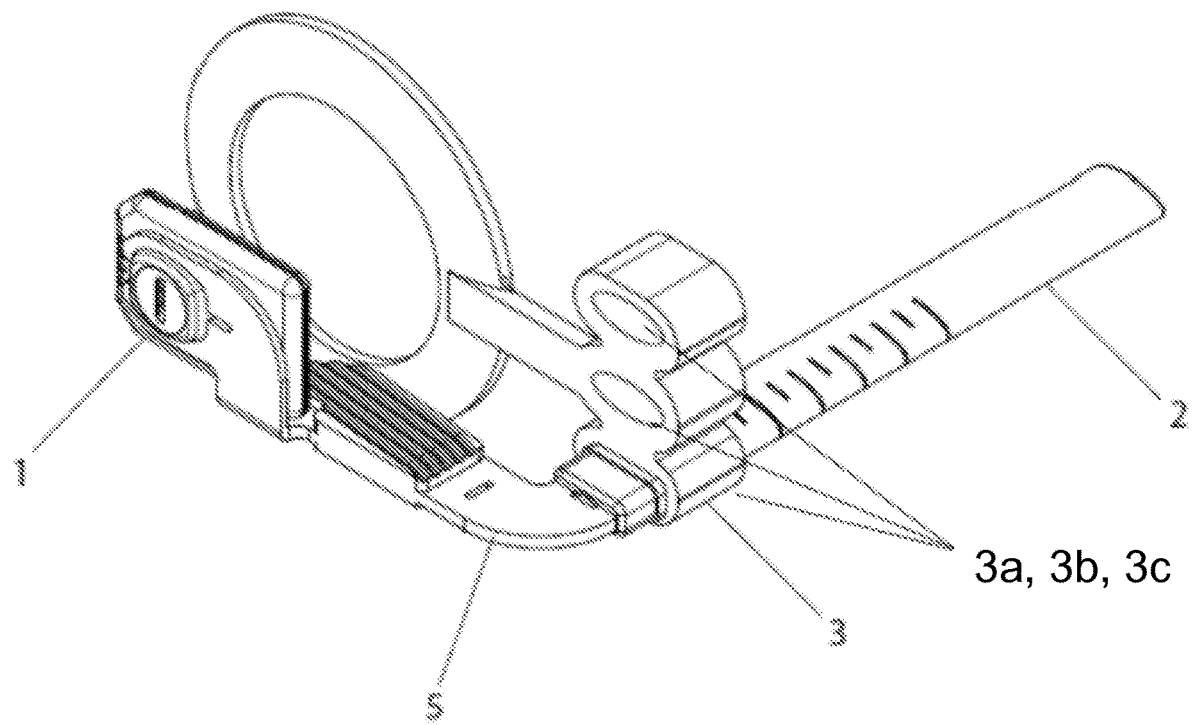
FIG. 7 shows a posterior holder holding the wireless intraoral sensor in accordance with certain embodiments.

FIG. 7 shows the holder suitable for the maxillary posterior position. The handle 2 and x-ray tube alignment ring 3 are the same as before. However as noticed earlier the ring 3 is provided with three separate slide through positions 3a, 3b and 3c in order to allow for posterior maxillary, bite wing or posterior mandibular imaging position of the sensor. The bite block 5 in FIG. 7 corresponds to the posterior imaging position and as shown position 3a is used for sliding through the handle. Critically once again in accordance with certain embodiments the WIOS 1 is held in place from the battery hump, thus making for a comfortable and painless positioning of the sensor inside the human mouth cavity. There is no part of the holder or the brackets or any other part that is in front of the active imaging area or around any of the edges. As before ridges are provided on the posterior bite block to facilitate secure biting onto the bite block when in position.

Figure 8:
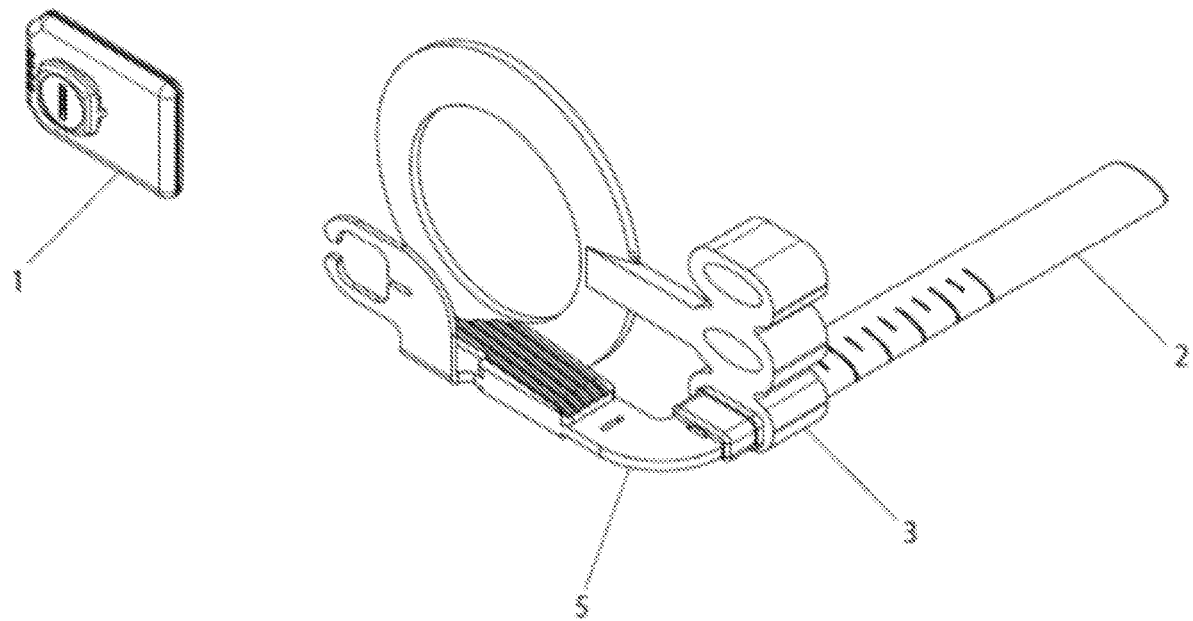
FIG. 8 shows the posterior holder and separately the wireless intraoral sensor in accordance with certain embodiments.

FIG. 8 is same as FIG. 7 except that the WIOS 1 is shown removed from the holder.

Figure 9:
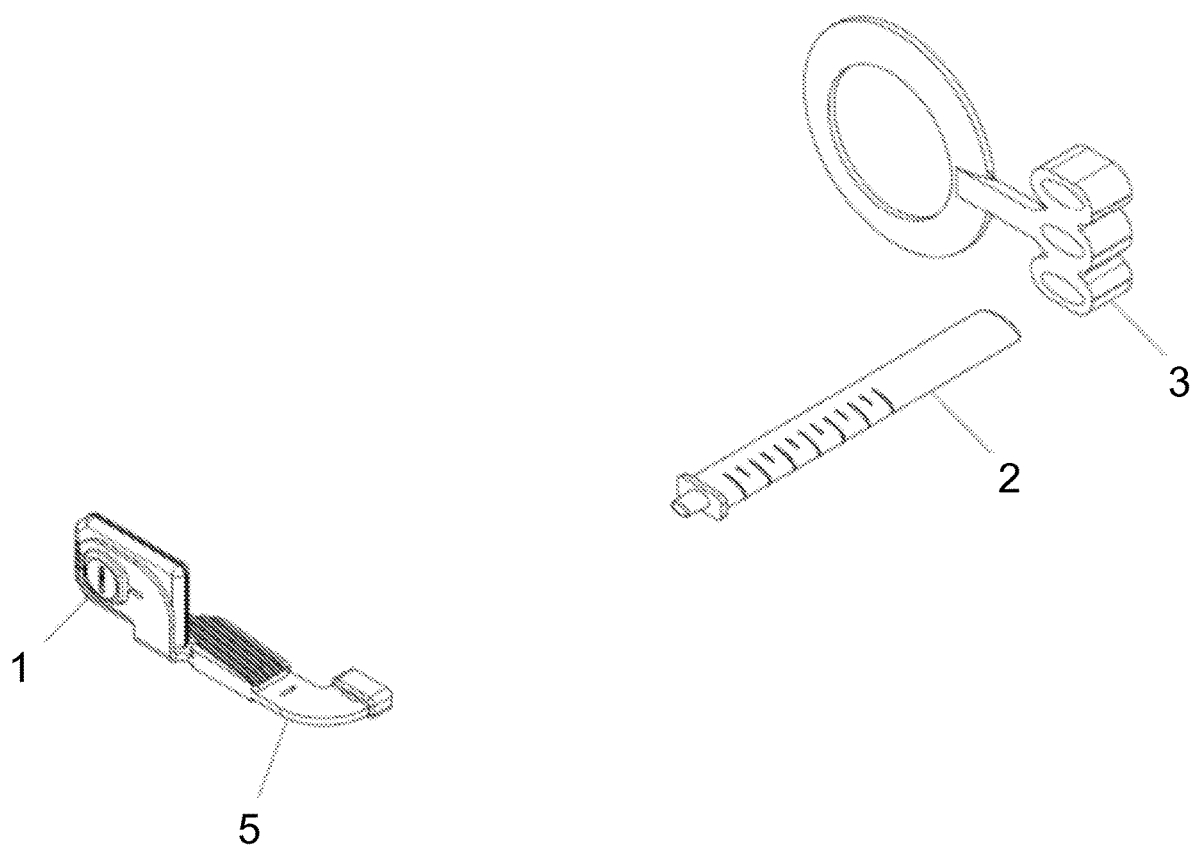
FIG. 9 shows the posterior holder of the wireless intraoral sensor disassembled to its various parts in accordance with certain embodiments.

FIG. 9 is similar to FIG. 8, with the holder disassembled to its three constituent parts: the handle 2, the ring 3 and the bite block 5. The WIOS 1 is shown mounted onto the posterior bite block piece 5. The bite block piece in FIG. 9 or in any of the previous figures can be autoclavable or can be a disposable material.

Figure 10:
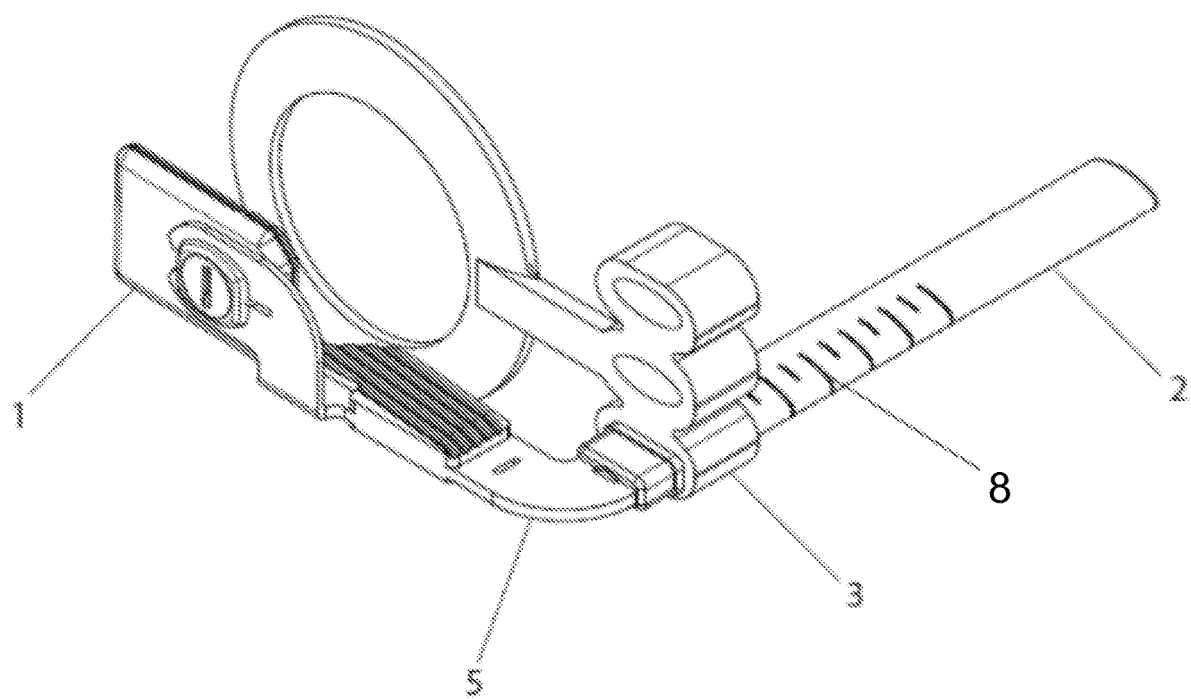
FIG. 10 shows the posterior holder holding the wireless intraoral sensor rotated 180° (180 degrees; i.e. the truncated corners are pointing inbound and towards the bite block) in accordance with certain embodiments.

FIG. 10 is similar to FIG. 7, showing the holder with the posterior bite block, however once again the WIOS 1 has been rotated (reversed) 180 degrees with the truncated corners pointing inwards and towards the posterior bite block 5. Furthermore the handle 2 has measuring notches 8, i.e. indentations or incisions on the surface of handle 2 such that the x-ray tube alignment ring 3 can be positioned a certain distance from the WIOS 1 active area. In FIG. 10 the position of the ring 3 is as innermost as practically foreseeable and this corresponds to approximately 2.5 cm from the active area of the WIOS 1. The handle offers a variety of positions and nominally the average position would place the ring at about 5 cm (shown with numeral 8 in FIG. 10) from the active face of the WIOS 1.

Figure 11:
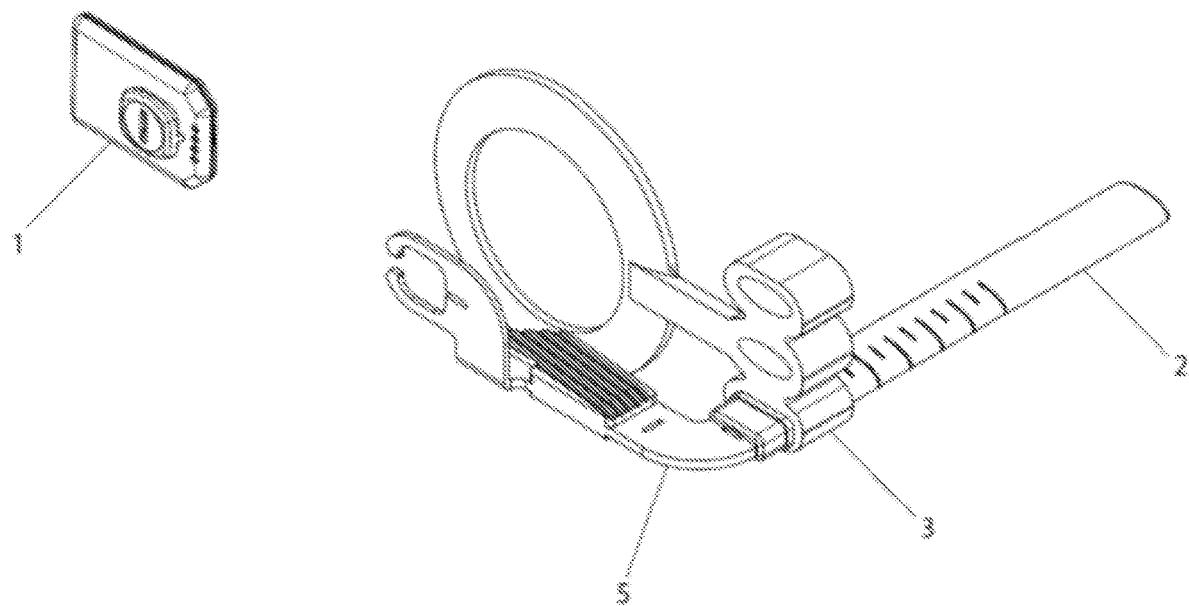
FIG. 11 shows the posterior holder and separately the wireless intraoral sensor rotated 180° (180 degrees; i.e. the truncated corners are pointing inbound and towards the bite block) in accordance with certain embodiments.

FIG. 11 shows the holder with the posterior bite block and the WIOS 1 rotated 180 degrees (reversed) and detached from the posterior bite bock.

Figure 12:
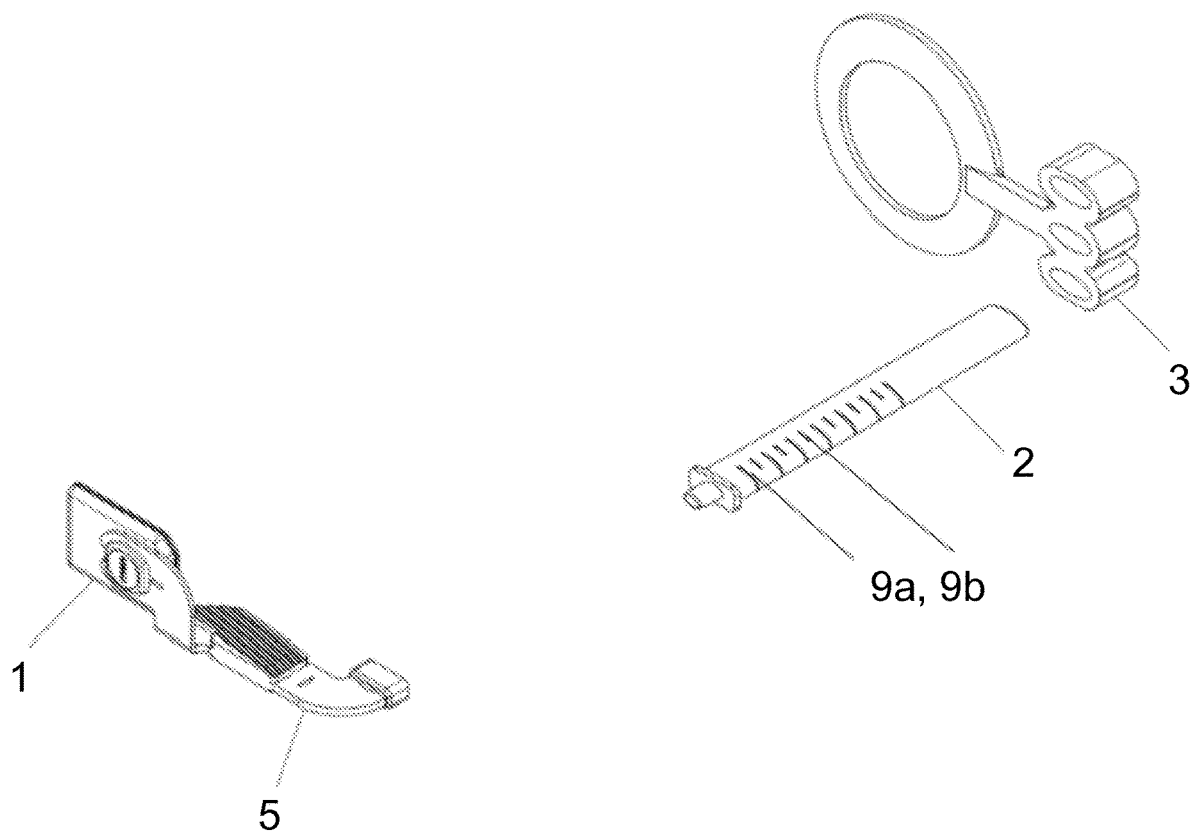
FIG. 12 shows the posterior holder, of the wireless intraoral sensor rotated 180° (180 degrees; i.e. the truncated corners are pointing inbound and towards the bite block), disassembled to its various parts in accordance with certain embodiments.

FIG. 12 shows the holder with the posterior bite block disassembled and the WIOS rotated (reversed) 180 degrees.

The handle 2 includes as in all previous Figures measuring notches. The nearest notch 9a corresponds to 2.5 cm distance between the ring face (when assembled) and the WIOS 1 active area and notch 9b corresponds to 5 cm distance.

Figure 13:
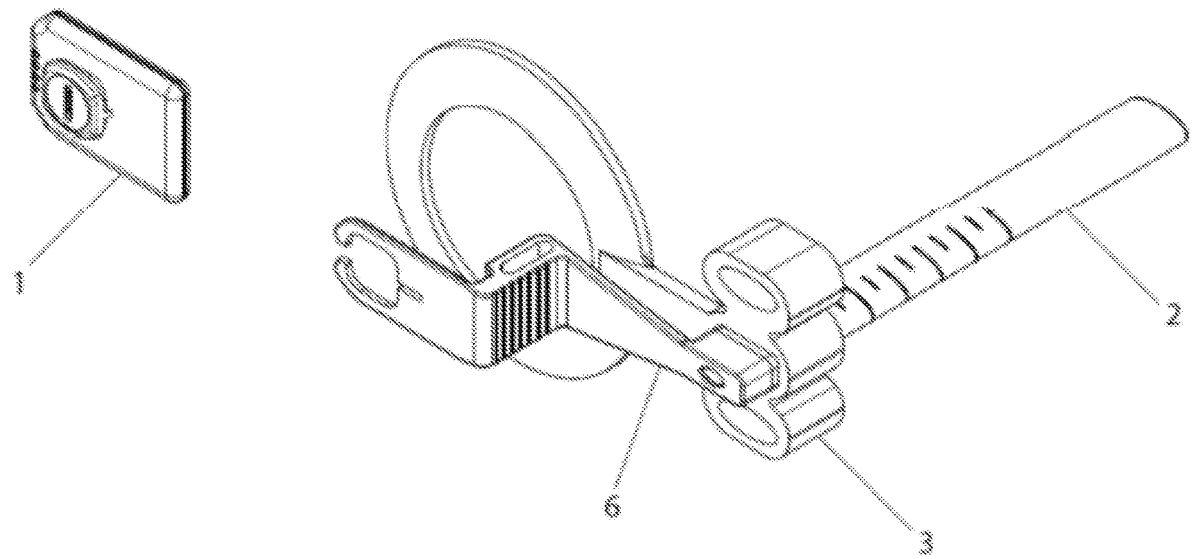
FIG. 13 shows an anterior holder and separately the wireless intraoral sensor in accordance with the certain embodiments.

FIG. 13 shows the WIOS 1 holder in accordance with certain embodiments and the anterior bite block 6. WIOS 1 is detached from the bite block in FIG. 13 while in FIG. 14 the WIOS 1 is mounted onto the anterior bite block 6. The mounting is achieved as in all previous cases utilizing the battery hump on the back of the WIOS 1. A bracket part 5 clips onto the groove 102 provided on the WIOS battery hump 105 (FIG. 1c), guided by the location feature 103 (FIG. 1c) which fits, slides a bit and clips into a corresponding recess 7 provided on 5.

Figure 15:
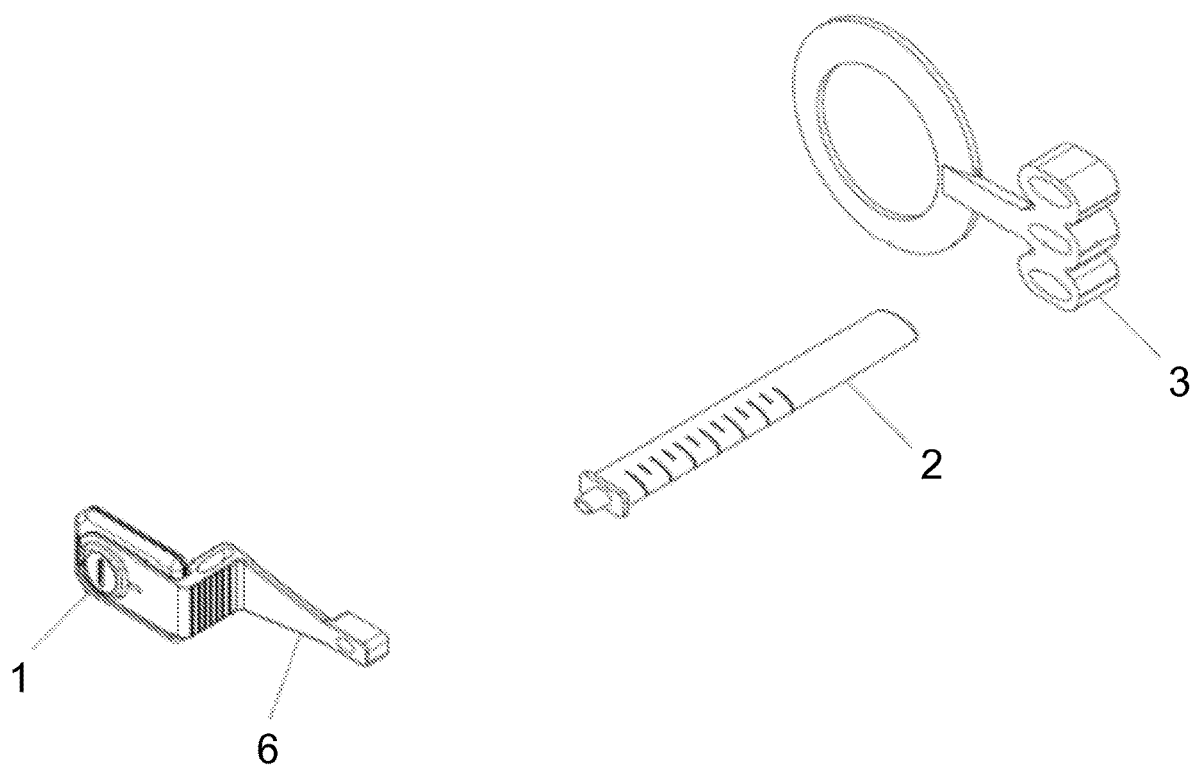
FIG. 15 shows the anterior holder of the wireless intraoral sensor disassembled to its various parts in accordance with certain embodiments.

FIG. 15 shows the WIOS holder in accordance with certain embodiments disassembled into its three main parts.

Figure 14:
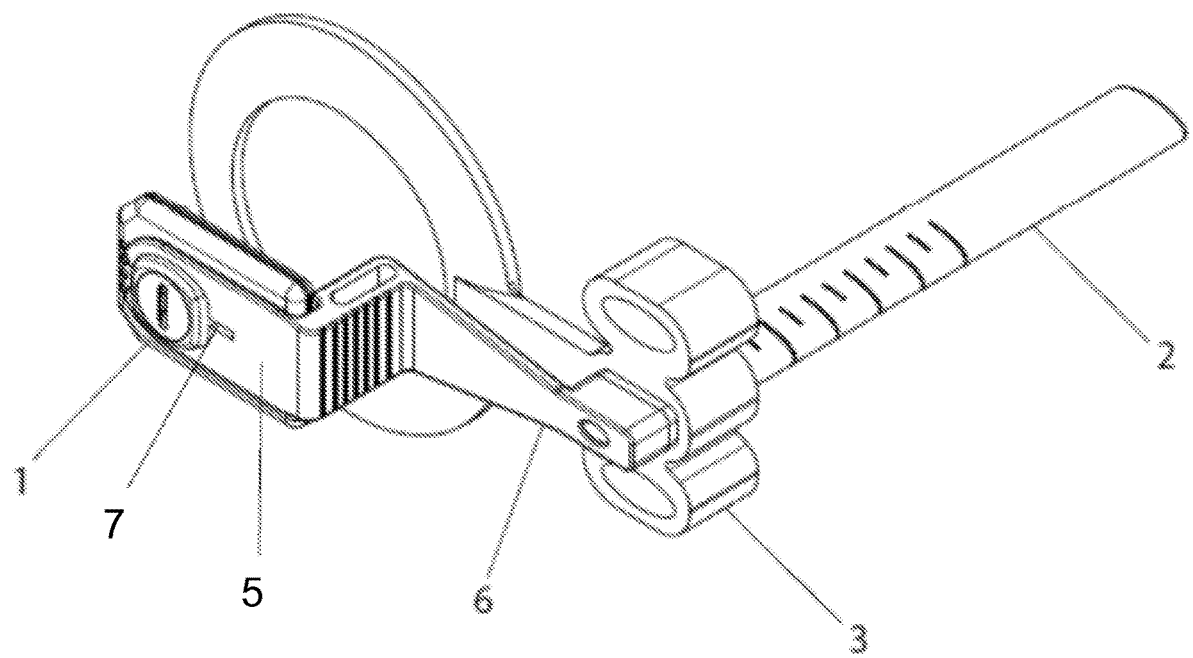
FIG. 14 shows the anterior holder holding the wireless intraoral sensor in accordance with certain embodiments.
Figure 16:
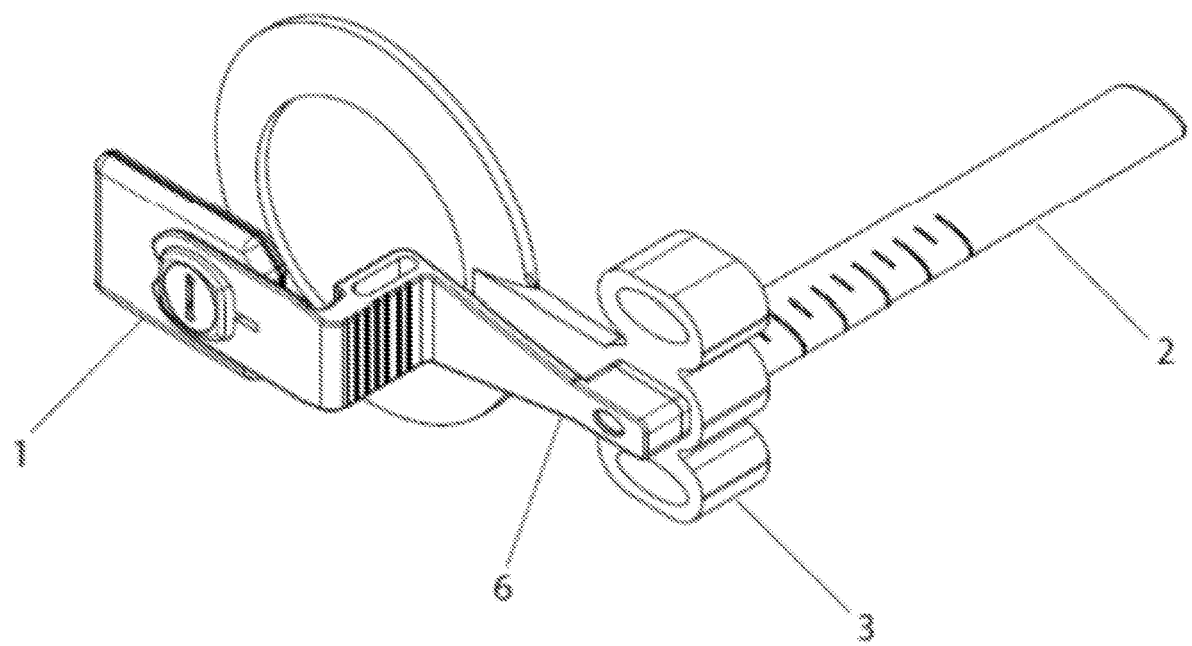
FIG. 16 shows the anterior holder holding the wireless intraoral sensor rotated 180° (180 degrees; i.e. the truncated corners are pointing inbound and towards the bite block) in accordance with certain embodiments.

FIG. 16 is similar to FIG. 14, with the WIOS 1 however rotated (reversed) 180 degrees. As can be seen from the FIG. 16 the truncated corners and corresponding WIOS 1 edge do not come into contact in this position with the bottom of the anterior bite block thus offering the extra flexibility and versatility to image different parts of the human cavity in the anterior region without causing pain or discomfort. This flexibility is achieved by not having the battery hump in the middle of the long dimension on the backside of the WIOS. Therefore, when rotated 180 degrees and then mounted onto the anterior bite block the WIOS is shifted upwards and away from the bottom 6a of the anterior bite block.

Figure 17:
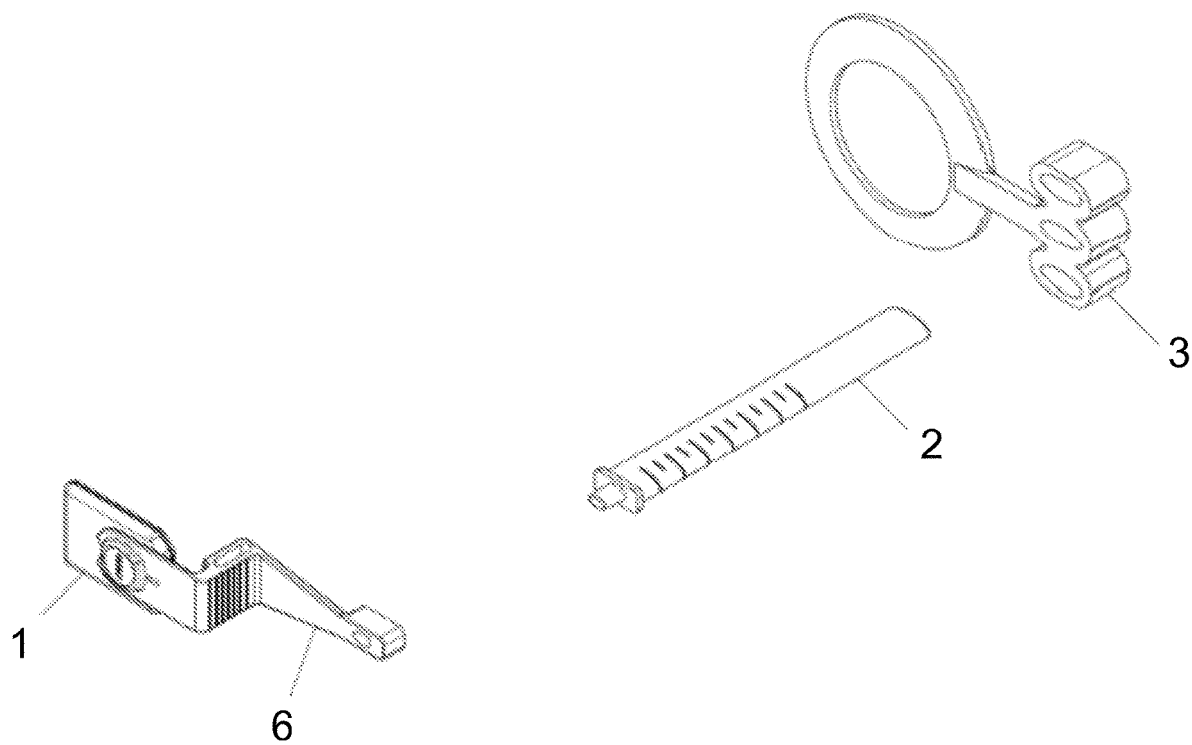
FIG. 17 shows the anterior holder, of the wireless intraoral sensor rotated 180° (180 degrees; i.e. the truncated corners are pointing inbound and towards the bite block), disassembled to its various parts in accordance with certain embodiments.

FIG. 17 is like FIG. 16 with the three parts of the holder shows separately.

Figure 18:
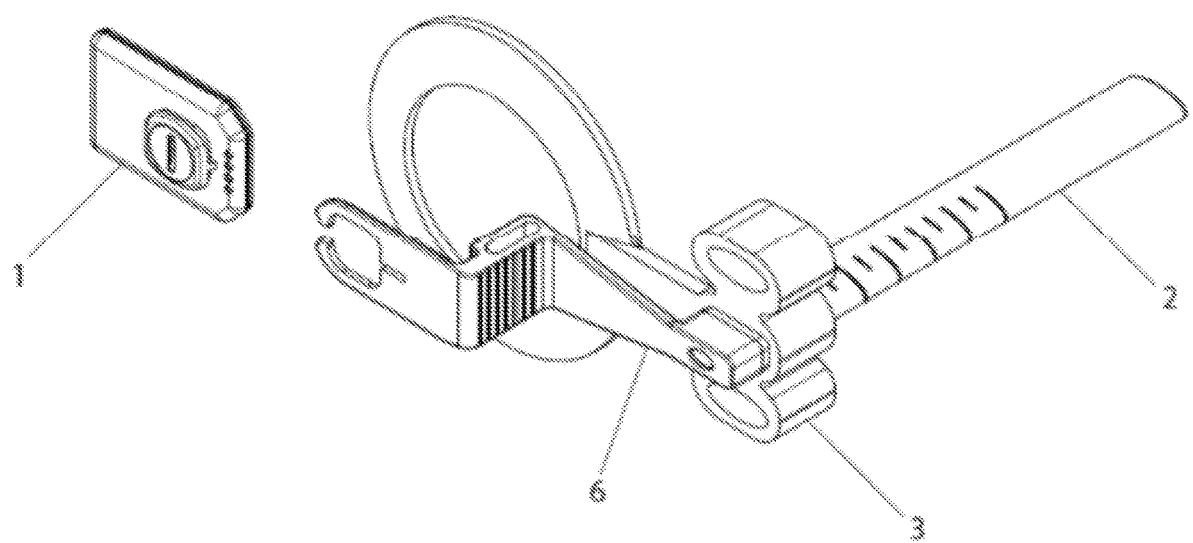
FIG. 18 shows the anterior holder and separately the wireless intraoral sensor rotated 180° (180 degrees; i.e. the truncated corners are pointing inbound and towards the bite block) in accordance with the certain embodiments.

FIG. 18 is like FIG. 16 with the WIOS 1 detached from the anterior bite block.

Figure 19:
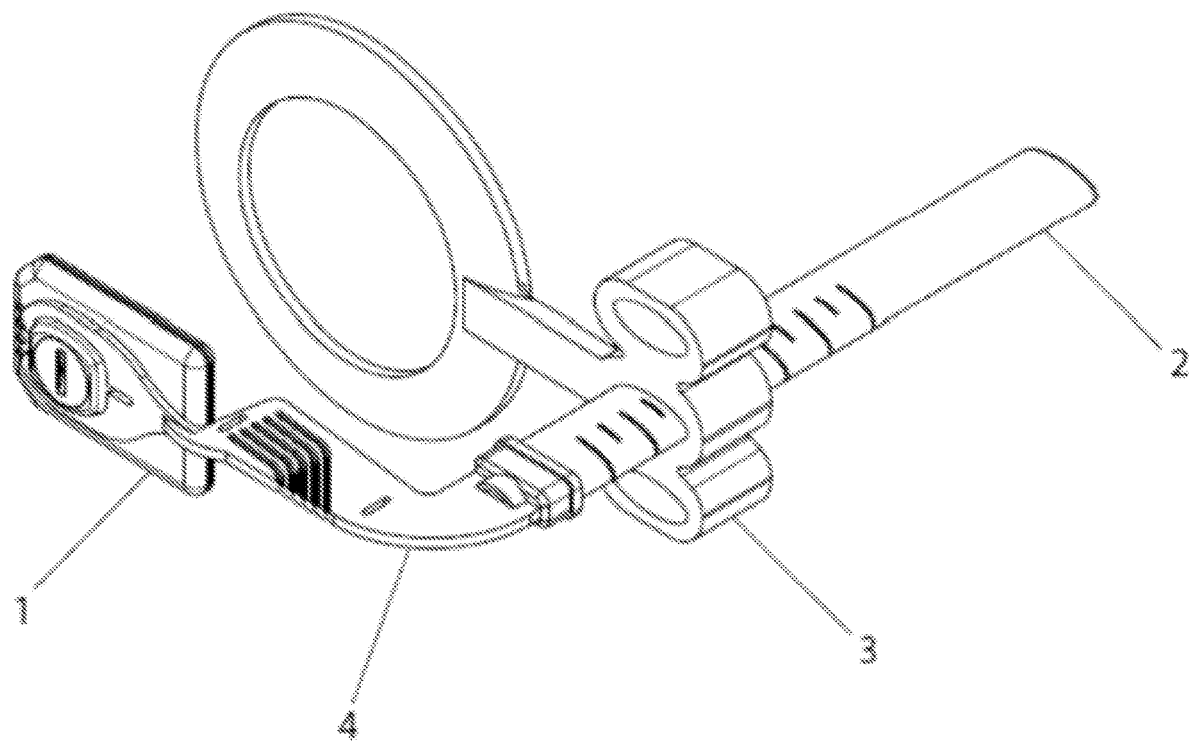
FIG. 19 shows the bite wing holder with the x-ray tube alignment ring at 50 mm distance from the wireless intraoral sensor in accordance with certain embodiments.

FIG. 19 shows the WIOS holder with the bite wing block in accordance with certain embodiments and the alignment ring 3 in position at a distance of 5 cm (50 mm) from the active face of the WIOS 1.

Figure 20:
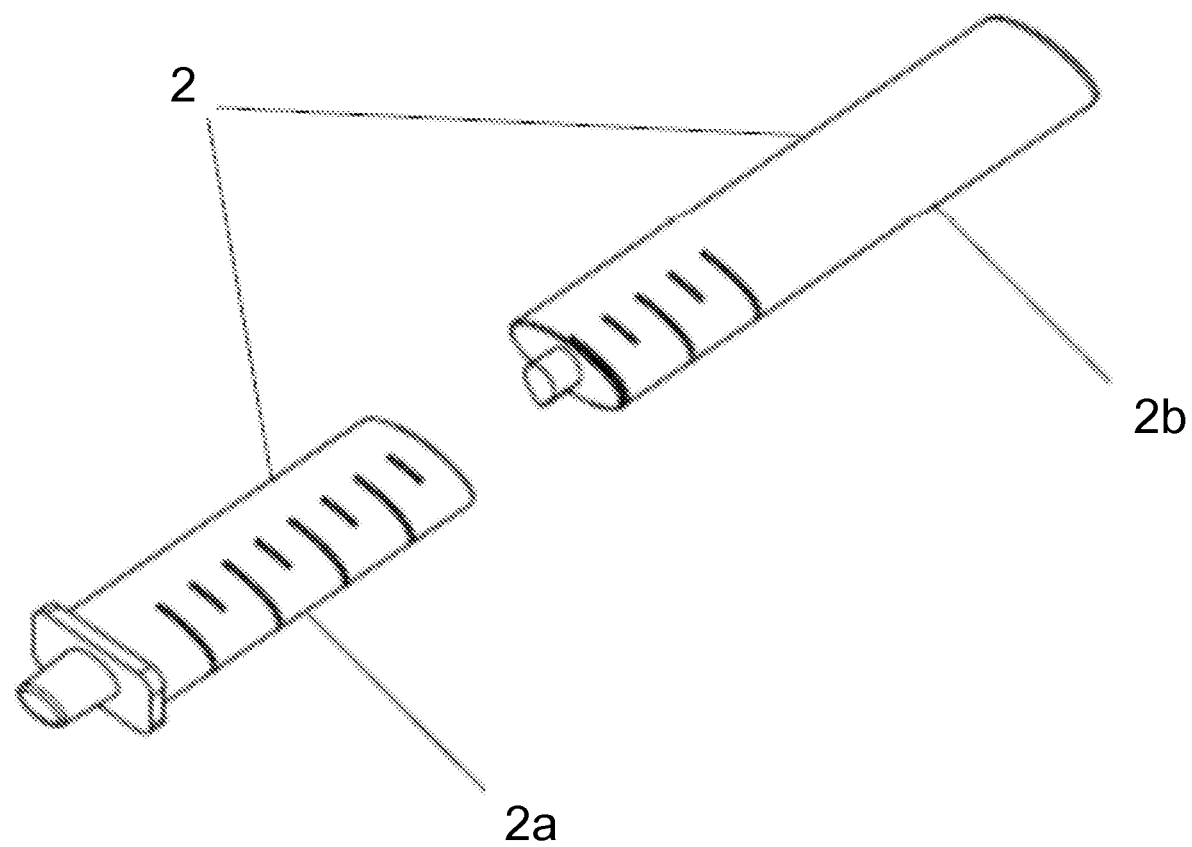
FIG. 20 shows the handle of any of the holders previously shown, comprising two separate parts.

FIG. 20 shows the handle 2 of the WIOS 1 holder in accordance with any of the previous Figures, however the handle 2 comprises two separate parts 2a and 2b. Part 2a alone can be used in situations where one is using a mobile x-ray source where the space available would not allow the full length of the handle 2 to be used, because of the shielding plate around the short cone of such mobile x-ray tubes. Usually in mobile x-ray tubes the focal spot to alignment ring 3 distance is much smaller and typically in the range of 15 cm to 25 cm and a shielding plate surrounds the short cone. In accordance with certain embodiments the handle 2 is modular and is made of two parts 2a, suitable for such short cone x-ray tube applications and 2b which when connected with part 2a allows the handle and holder to be used in the conventional (long cone) x-ray tube which are typically on a self-standing base or wall mounted and have a focal spot to alignment ring 3 distance of approximately 30 cm. The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means without deviating from the characteristics of the invention.

Furthermore, some of the features of the above-disclosed embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

The invention claimed is:

1. A wireless intraoral x-ray imaging sensor holder comprising a bite block configured to attach to a hump on the backside of a wireless intraoral x-ray imaging sensor, said wireless intraoral x-ray imaging sensor configured without a cable coming out from the sensor and wherein said hump corresponds to encapsulation of a battery of said wireless intraoral x-ray imaging sensor.

2. A wireless intraoral x-ray imaging sensor holder according to claim 1 further comprising a holder handle and an x-ray tube alignment ring.

3. A wireless intraoral x-ray imaging sensor holder according to claim 2 wherein said holder handle comprises separately a first part and a second part, whereas said first part can be selectively used individually for reducing the overall length of handle or in the alternative said first part and second part are selectively used combined together for increasing the overall length of handle.

4. A wireless intraoral x-ray imaging sensor system, comprising
a wireless intraoral x-ray imaging sensor comprising a battery a hump on the backside of said wireless intraoral x-ray imaging sensor, wherein the hump encapsulates a battery and the sensor is configured without a cable coming out from the sensor; and
a wireless intraoral x-ray imaging sensor holder for securing and positioning said wireless intraoral x-ray imaging sensor,
wherein said holder secures in place said wireless intraoral x-ray imaging sensor from the hump.

5. A wireless intraoral x-ray imaging sensor system according to claim 4, wherein said wireless intraoral x-ray imaging sensor is selectively secured onto said wireless intraoral x-ray imaging sensor holder with two or more orientations.

6. A wireless intraoral x-ray imaging sensor system according to claim 5, wherein said wireless intraoral x-ray imaging sensor is secured onto said wireless intraoral x-ray imaging sensor holder selectively, with two orientations, 180 degrees with respect to each other.

7. A wireless intraoral x-ray imaging sensor holder comprising a bite block configured to attach to a hump on the back of the wireless intraoral x-ray imaging sensor, wherein the bite block is a posterior bite block, wherein said wireless intraoral x-ray imaging sensor is configured without a cable coming out from the sensor, and wherein said hump corresponds to encapsulation of a battery of said wireless intraoral x-ray imaging sensor.

8. The wireless intraoral x-ray imaging sensor holder according to claim 7 wherein said wireless intraoral x-ray imaging sensor is selectively secured onto said posterior bite block with two or more orientations.

9. A wireless intraoral x-ray imaging sensor holder comprising a bite block configured to attach to a hump on the back of the wireless intraoral x-ray imaging sensor, wherein the bite block is an anterior bite block, wherein said wireless intraoral x-ray imaging sensor is configured without a cable coming out from the sensor, and wherein said hump corresponds to encapsulation of a battery of said wireless intraoral x-ray imaging sensor.

10. A wireless intraoral x-ray imaging sensor holder according to claim 9 wherein said wireless intraoral x-ray imaging sensor is selectively secured onto said anterior bite block with two or more orientations.

11. A wireless intraoral x-ray imaging sensor holder comprising a bite block configured to attach to a hump on the back of the wireless intraoral x-ray imaging sensor, wherein the bite block is a bite-wing bite block wherein said wireless intraoral x-ray imaging sensor is configured without a cable coming out from the sensor, and wherein said hump corresponds to encapsulation of a battery of said wireless intraoral x-ray imaging sensor.

12. A wireless intraoral x-ray imaging sensor holder according to claim 11 wherein said wireless intraoral x-ray imaging sensor is selectively secured onto said bite-wing bite block with two or more orientations.

13. A wireless intraoral x-ray imaging sensor system according to claim 4, wherein said hump is provided with at least one groove configured to attach to a bite block.

14. The wireless intraoral x-ray imaging sensor holder according to claim 1 wherein the hump corresponding to encapsulation of the battery comprises an edge of the hump that is at least 2 mm inwards from a nearest edge of the wireless intraoral x-ray imaging sensor.

15. The wireless intraoral x-ray imaging sensor holder according to claim 14 wherein the hump is centered along the short or the long dimension of the wireless intraoral x-ray imaging sensor.

16. The wireless intraoral x-ray imaging sensor holder according to claim 15 wherein the hump is centered along the short dimension of the wireless intraoral x-ray imaging sensor.

17. A wireless intraoral x-ray imaging sensor holder according to claim 15 wherein the hump is provided with a groove or an indent around at least part of the circumference so that the holder will hold the sensor from the hump utilizing said groove or said indent.

* * * * *